United States Patent [19]

Potter

[11] 4,116,045
[45] Sep. 26, 1978

[54] OIL DETECTOR

[76] Inventor: Bronson M. Potter, R.F.D. 1, Greenville, N.H. 03048

[21] Appl. No.: 752,199

[22] Filed: Dec. 20, 1976

[51] Int. Cl.$^2$ ............................................. G01N 27/18
[52] U.S. Cl. ............................ 73/61.1 R; 23/230 HC; 73/295; 340/605; 340/622
[58] Field of Search ...................... 73/61.1 R, 53, 204, 73/295; 324/65 R; 340/244 R; 23/230 HC

[56] References Cited

U.S. PATENT DOCUMENTS

| | | | |
|---|---|---|---|
| 3,181,557 | 5/1965 | Lannan, Jr. | 73/295 X |
| 3,432,840 | 3/1969 | Neapolitakis et al. | 340/244 R |
| 3,449,942 | 6/1969 | Simon | 73/53 |
| 3,548,637 | 12/1970 | Wicks | 73/53 |
| 3,600,946 | 8/1971 | Ziemba et al. | 73/295 |
| 3,712,116 | 1/1973 | Andre | 73/61.1 R X |
| 3,719,936 | 3/1973 | Daniels et al. | 340/236 |

OTHER PUBLICATIONS

Power, A. D. *An Indicator for the Level of Liquids*, in Review of Scientific Instruments, p. 188, Jun. 1943.

*Primary Examiner*—Richard C. Queisser
*Assistant Examiner*—Joseph W. Roskos

[57] ABSTRACT

Detecting different fluids, such as oil at the surface of water, by a heated monitoring element exposed for contact with the fluid, the element having a resistance characteristic that changes as a function of temperature, in preferred embodiments being the mere filament of a light bulb. One system employs circuitry for periodically applying a pulse of electrical heating current to the monitoring element, to heat and produce a change in its electrical resistance, and output circuitry responsive to change in electrical resistance to indicate the nature of the fluid. In another system the resistance of the monitoring element is controlled by comparison to a constant reference, the heating current required serving to indicate the nature: e.g. oil, water or air, of the fluid contacting the element. Features of the invention include positioning the monitoring element at a liquid-air interface by a buoyant member, preferably with means to cause the element to transit the interface prior to a detection cycle; a driver supported on a housing, effective to move the element to produce this motion; circuitry for passing heating current through the monitoring element to clean its exposed surface of oil; and circuitry for limiting the electrical parameters of the cleaning current to prevent ignition of oil.

26 Claims, 10 Drawing Figures

OIL DETECTOR

This invention relates to systems for discriminating between fluids as for detecting and signalling the presence of oil on the surface of water or the like.

For control of oil pollution of water or for oil leaks a need exists for a practical, low cost device to detect the presence of oil in small quantities. Expensive and complicated, and in some cases, unreliable, methods have been previously used such as measuring the reflectivity of the fluid surface or measuring the response of the fluid to a high frequency electromagnetic wave, or selectively collecting a quantity of oil and detecting it on the basis of weight, or determining thermal conductivity from a heated probe. An object of this invention is to provide an oil detection system that is inexpensive, reliable and versatile, and in particular, to provide an oil detection system capable even of detecting thin films of oil, of operating with low power, of being so inexpensive as to permit use e.g. in sumps adjacent small volume oil storage sites, and of permitting continued use after once having detected the presence of oil. (The term "oil" as used here refers to fluids immiscible in and lighter than, or at least having a markedly different heat transfer characteristic than, water, e.g., hydrocarbons such as crude petroleum and distillate products, and animal or vegetable oils and other liquids.)

The invention is of the thermal conductivity type employing a monitoring element that has a surface exposed for contact with the fluid to be monitored, e.g. contacting oil if present, otherwise water. The monitoring element has a resistance characteristic that changes as a function of temperature, and when heated, its temperature varies dependent upon the presence of oil or water due to differences in specific heat and thermal conductivity of oil and water.

According to one aspect of the invention, by applying a short pulse of electrical heating current to the monitoring element, as by triggering a silicon control rectifier to discharge a capacitor, a different decay rate in the electrical resistance-time curve is produced, dependent upon presence of oil or water at the element. By thereupon sensing resistance as by a bridge circuit, using a reference element assuredly contacting water and similarly heated in synchronism by a short heating current pulse, an output indication of oil is produced. This output may be used to power a loudspeaker or alerting device, or in digital form, to serve as an input to warning or control logic which operate on the aggregate input of a number of such signals. The low power requirement of the instrument permits continual use and makes battery-powered units feasible.

According to another aspect of the invention, it is realized that a product of long-existing technology, of insignificant expense, the common light bulb, leads to an excellent oil-water monitor. As a monitoring element, the metal filament provides low mass and large surface area which, with a heating pulse of short duration, provides an accurate indication due to a steeply sloping resistance vs. temperature characteristic, doing so with extremely low consumption of electrical power. The surrounding glass envelope of a light bulb is employed with the reference element, for providing a strong means holding water, to assure filament-water contact of the reference element. While the particular filament may be made of various metals, tungsten wire made as a simple electric light bulb filament is preferred.

The size and configuration of the filament is determined by factors related to the particular application such as mechanical stability, electrical efficiency, ease of cleaning, and cost. In general, wire sizes in the range of about 0.001 to 0.05 inch may be used, the lower limit being a function of the mechanical strength (fragility) of the filament and the upper limit being a function of size of the unit, sensitivity, and electrical power consumption considerations.

In certain instances a large straight filament may recover from oil contamination more easily than a small filament (it is more difficult to dislodge oil that entirely surrounds the wire than mere spots of oil on the wire) but the large filament is less sensitive and has less electrical efficiency than the small filament. Small diameter wires are easily wound in helices (of about 10 wire diameters in diameter) and provide large thermal metal-fluid heat transfer interface in small volume. Systems employing wire of small diameter also produce readings of less ambiguity, particularly in monitoring lighter hydrocarbons such as gasoline.

Another important feature of the invention concerns the discovery that the simple metal filament, once covered with oil, can be reliably cleaned by a relatively long duration of controlled heating current, without creating a fire or explosion hazard. The heat reduces the viscosity of the oil and its surface tension, and produces thermal agitation at the interface with surrounding fluid, with vaporization, cavitation and sonic cleaning effects, the filament even "growls", all of which contribute to freeing the filament surface of oil contamination. The magnitude of the heating effect is subject to current and resistance limiters, which protect the filament and prevent it from causing ignition of the oil. Thus, effective cleaning by application of heating current can be accomplished while the device remains on station, to ready the device to repeat its detection function.

In important embodiments the element is arranged to transit the surface to enable coating of the filament when oil is present for detection and removal of oil on the detector by lavage, when the oil slick is gone. Preferred embodiments take the form of a bobbing buoy-like device and a positively driven unit.

In a preferred oil detection system for detecting even very thin films of oil, the monitoring filament is mounted on a float and connected in circuit with a reference filament, both being simultaneously and rapidly heated periodically by short pulses of electrical current from a single source. The changes in resistance of the monitoring and reference filaments due to the electrical heating pulse are compared and presence of oil is indicated by a differential change in resistance of the two filaments, resulting in a pulsed or digital output, should oil be present, of frequency corresponding to the frequency of the heating pulses. The comparison circuitry may take a variety of forms including, for example, differential amplifier circuitry. A bridge circuit provides a simple and reliable comparison circuit. Detection systems in accordance with the invention may employ monitoring, reference, heating and comparison components that are cheap, simple and rugged. Several detection units can be provided to monitor redundantly a particular area, with detection based upon statistical analysis of the output of the units, or the detection system may be employed with a weir or an oil collecting system to increase the system sensitivity.

In one preferred embodiment, detection and reference cells are mounted on a rotatable support, the reference cell being disposed in an ampule (e.g. the light bulb) partially filled with reference fluid. Two positions of rotation provide for increased sensitivity in determining the presence of oil, one position in which both elements are totally immersed, the monitoring element in the liquid being monitored, the reference cell in the liquid of the ampule; the other position in which both elements are exposed to air, the reference element having a water film on it, the monitoring element an oil film, if oil be present at the surface being monitored.

In embodiments in which the sensitivity of detection is enhanced by use of such dual mode, immersed and air, operation, a simple water detection device, e.g. a piezoelectric vibrating element or a heated probe, is exposed to water or air to produce an indication of the media to which the monitoring element is exposed, this indication ensuring proper categorization of the signal from the monitoring element.

In arrangements in which the monitoring element transits the air-liquid interface, picking up an oil film, while the reference element is totally immersed, means are provided to ensure that the comparison between reference and monitoring elements occurs under equivalent conditions. Predetermined selection of the waterline, detection or positive control of the totally immersed condition of the monitoring element and statistical analysis of the output pulse train are preferred means to ensure this.

According to another aspect of the invention a system for detecting different fluids such as oil at the surface of water is provided comprising a monitoring element as before, circuitry for applying electrical heating current to the monitoring element to heat and produce a change in electrical resistance of the monitoring element, means for limiting the amount of change of resistance developed, and output circuitry responsive to the current through the element to indicate the nature of the fluid in contact with the exposed element.

In preferred embodiments the circuit includes a substantially constant reference resistance and means for applying heating current to the monitoring element until its resistance is balanced relative to the reference resistance. Preferably an amplifier is adapted to apply current through the reference and monitoring elements and means are provided responsive to differential current flow therethrough to regulate the amplifier, thereby to control current through the monitoring element.

These and numerous other features and advantages will be further understood as the following description or particular embodiments progresses, in conjunction with the drawings, in which:

FIG. 1 is a perspective view of an oil detection system according to the invention; while

FIG. 5 is a view similar to FIG. 1 of another embodiment, while

DESCRIPTION OF PARTICULAR EMBODIMENTS

Figure 1:
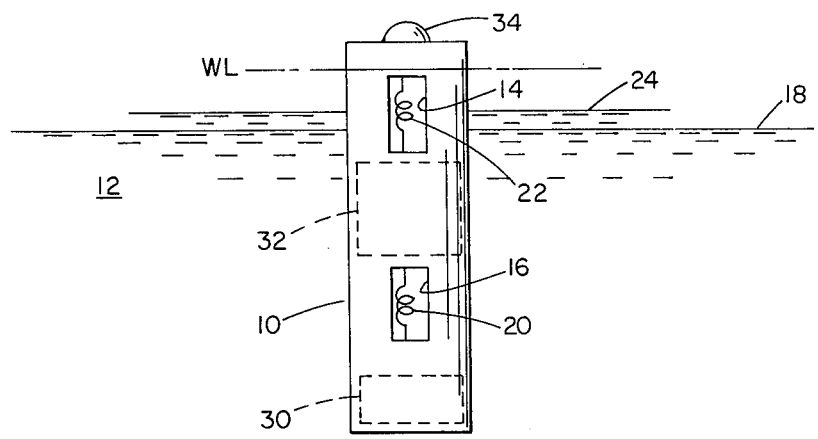

Referring to FIG. 1, the oil detection system includes a buoyant, tubular housing 10 designed to float on water 12 to be monitored. Housing 10 has upper and lower recesses 14, 16. The buoyancy of housing 10 is such that recess 14 is disposed at the surface 18 of the water and recess 16 is submerged. A tungsten reference filament 20 is disposed in recess 16 so that it remains under water. A monitoring filament 22 is disposed in recess 14 at the water surface 18 so that it is exposed for coating with oil should a film of oil 24 exist on the monitored surface 18 (film 24 which may be grossly exaggerated in thickness in FIG. 1). The oil detection unit may be self-contained and include batteries 30 (which function as ballast), electronics 32, and an output indicator 34 on its upper surface. In another embodiment, the unit may be connected by flexible cable (not shown) to a remote power supply and to remote output indicator circuitry.

The particular relationship of the monitoring element to the surface can vary, the relationship depending upon the conditions expected for use, i.e. whether the unit is to be installed in a quiescent pond or a very still sump or monitor bore at an oil storage site, or at the outfall of an industrial plant, or exposed to wave conditions as on the high seas. In the embodiment of FIG. 1, exposed to continual bobbing conditions, the at rest waterline WL is placed slightly above the monitoring filament 22, in such a position that normal bobbing will cause coverage of the filament with a film of oil, if oil be present, even if present as only a very thin layer on the water. The position of the normal waterline however ensures that statistically, over most of the time, the filament is completely immersed to establish approximately equal heat transfer conditions for the two filaments, except for the discrepancy introduced by the monitoring filament being coated with a thin film or being partly or wholly immersed in oil, should oil be present.

Figure 1A:
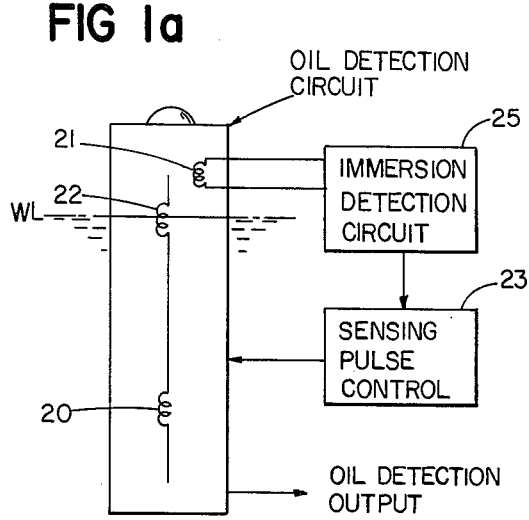
FIGS. 1a, 1b, 1c, and 1d are other preferred embodiments.

In the embodiment of FIG. 1a, the waterline WL is lower and a detector filament 21 is permanently energized. The filament 21 responds with higher resistance when immersed. This condition is detected by immersion detection circuit 25, which enables the heating pulse of the detection circuit. By this means the heating pulse is made to occur only when the monitoring filament is submerged.

Figure 1B:
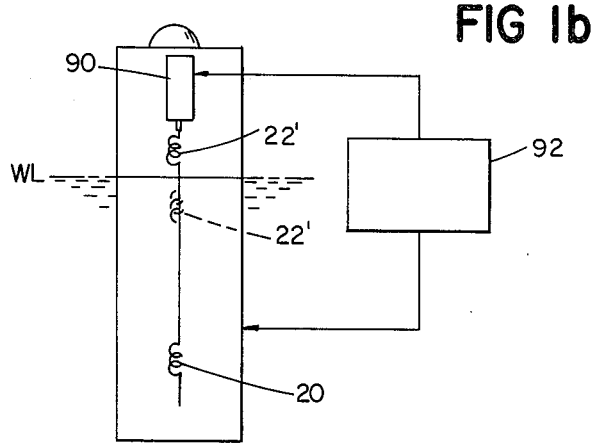

In the embodiment of FIG. 1b the monitoring element 22' is mounted at the end of a plunger of solenoid 90. In the retracted position the element lies above the waterline WL. When a detection cycle is desired the solenoid is energized by a control unit 92, to force the element to transit the air-liquid interface to pick up an oil film, and be submerged in liquid. Thereupon the control unit activates the heating pulse for the detection cycle.

Figure 1C:
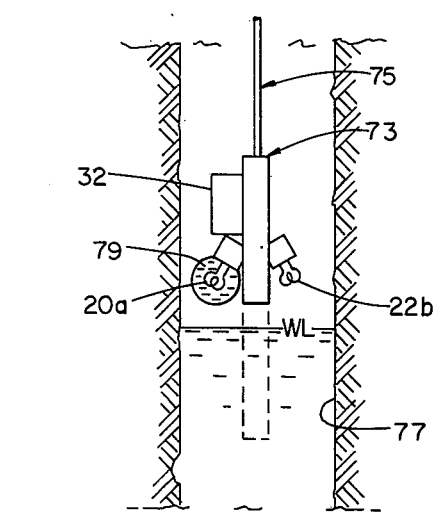

In the embodiment of FIG. 1c a probe 73 is suspended upon a supporting line 75 and lowered into a hole 77 bored for instance in the ground near an oil storage site. The probe includes as an integral unit an ampule 79, formed from a light bulb as mentioned previously, containing reference filament 20a, the volume filled with water, and on the other side, bare filament from a similar bulb, serving as a monitoring filament 22b. These filaments are connected in a monitoring circuit 32 such as that shown in FIG. 2. By lowering the probe 73 through the waterline provided by ground water level, the monitoring filament 22b receives a coating of any oil floating on the surface, while the filament 20a is protected by the ampule. After an interval permitting temperature equilibrium to be reached, the monitoring heating pulse is produced for heating the filaments and detection proceeds in the manner described.

Figure 1D:
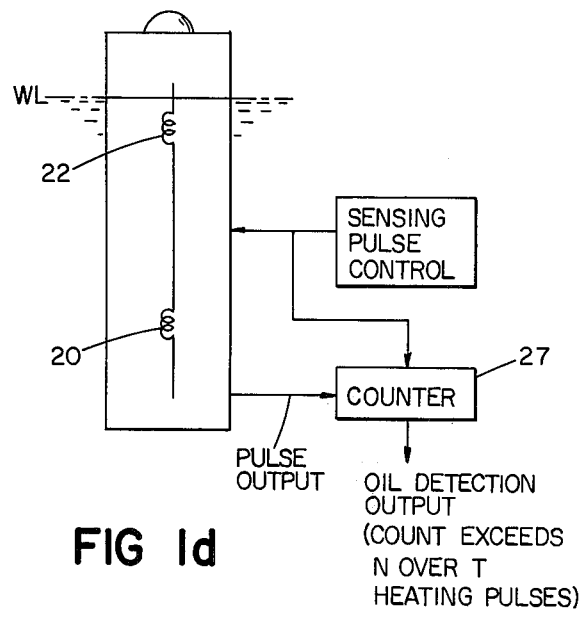

In the embodiment of FIG. 1d compensation is introduced to allow for partial exposure of the monitoring filament to air, by a statistical method. The oil detection pulses are counted over time by counter 27 and an oil detection output occurs only when a threshold number n of pulses is exceeded over a selected time frame, measured by a predetermined number T of heating pulses.

In still other embodiments both monitoring and reference filaments may be mounted to ensure that their exposure to liquid or air is balanced, as in FIGS. 3 and 4, again to ensure equivalent heat transfer conditions, as is often preferred.

Figure 2:
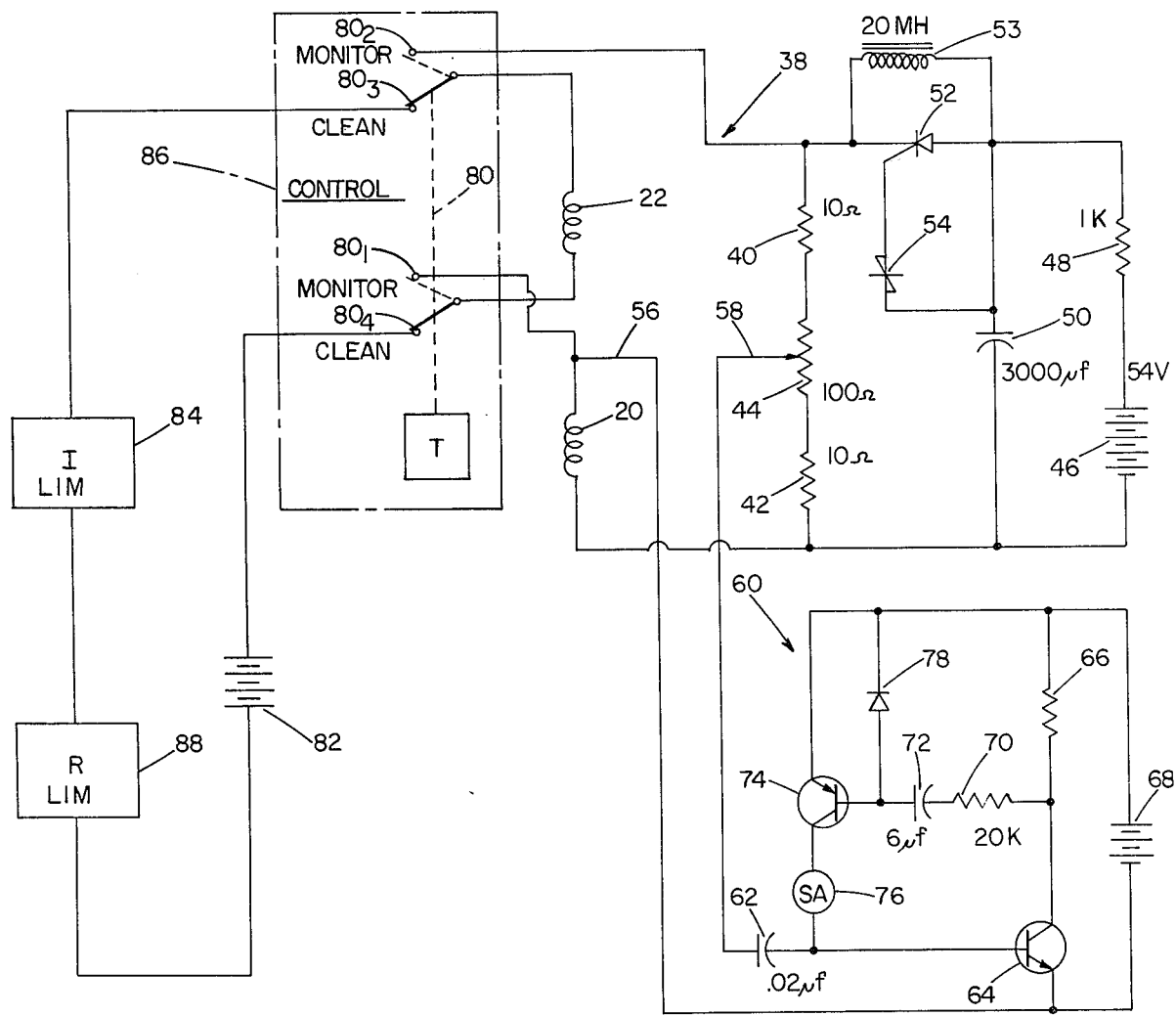
FIG. 2 is a schematic diagram of circuitry employed in the oil detection system of FIG. 1.

A schematic diagram of the electric circuit 32 in housing 10 is shown in FIG. 2. That circuit includes helical tungsten wire filament reference and monitoring elements 20 and 22 from electric light bulbs (for instance, for a modest detector, General Motors AC L1129, light bulb, 6 volt, 21 candle power). In one instance each filament is 1 inch in stretched length, of 0.004 inch diameter wire coiled in a 13 turn helix that is 0.2 inch long and 0.024 inch in diameter. Each filament has an electrical resistance at room temperature of less than 0.1 ohms. Monitoring filament 22 is switched between monitor circuit and clean circuit by double pole switch 80 of control unit 86. When contact is made with terminals $80_1$ and $80_2$ the monitor circuit is complete, the two filaments 20, 22 being connected in a bridge circuit with a series network of resistors 40 and 42, and potentiometer 44.

Connected to the bridge circuit is a current pulse generating circuit that includes a 54-volt battery 46, resistor 48, capacitor 50, silicon controlled rectifier 52, and semi-conductor controlled diode 54 that has a break down value of 38 volts. This circuit periodically applies to the bridge circuit a short pulse of heating current of high peak value which decays rapidly exponentially as the capacitor (of e.g. 3000 microfarad) is discharged, with effective heating time of the order of several milliseconds. The resistances of filaments 20 and 22 are a function of their heat dissipation characteristics, oil on the surface of filament 22 reducing its heat dissipation so that it becomes hotter or cools slower than reference filament 20, and its transient resistance becomes greater than the corresponding transient resistance of reference filament 20. This differential change in resistance produces a shift in the voltage at output line 56 relative to the voltage at output line 58 as an indication of the presence of oil on filament 22.

In operation of the circuit, capacitor 50 is charged by current flow through resistor 48, SCR 52 being non-conducting. When capacitor 50 is charged to about 38 volts, diode 54 breaks down into conducting condition and triggers SCR 52. Capacitor 50 then discharges through SCR 52 and the resistance circuit of the bridge filaments 20, 22 and resistors 40, 42 and 44. The short pulse of $\frac{1}{2}CV^2$ power (milliseconds in duration) flows primarily through the series circuit of filaments 20 and 22, producing a rapid temperature rise of those filaments. If the temperature dissipation characteristics of the two filaments are different — as is the case when oil is present on the surface of monitoring filament 22 — the transient resistance of filament 22 becomes greater than the transient resistance of filament 20, producing a voltage shift which is applied to detection circuit 60. SCR 52 turns off when capacitor 50 is discharged, and inductor 53 produces a reverse potential pulse. In either case the circuit resistance or resistance plus inductance, upon decay of the current from the capacitor, reduces holding current, effective to switch off the SCR 52 each time the capacitor is discharged. When capacitor 50 is recharged to the breakdown voltage of control diode 54, another pulse of heating current is applied to the bridge circuit, thus in a sense the circuit providing its own clock.

Detection circuit 60 is a monostable circuit which is triggered into conduction in response to a differential voltage that is generated when the resistance of filament 22 becomes greater than the resistance of filament 20 during the application of a monitoring pulse of heating current. That circuit includes coupling capacitor 62 connected to the base of transistor 64. Transistor 64 is connected in circuit with resistor 66 across battery 68. A timing network of resistor 70 and capacitor 72 is connected between the collector of transistor 64 and the base of transistor 74. An output device 76, which may be a Sonalert unit sold by P. R. Mallory and Co. Inc., is connected in the collector circuit of transistor 74. Transistor 64 is turned on in response to a voltage difference of predetermined magnitude between lines 56 and 58, and the resulting transition is coupled by resistor 70 and capacitor 72 to turn on transistor 74 so that output device 76 is energized and transistor 64 is driven into full conduction. Output device 76 is maintained energized until capacitor 72 is charged and transistor 74 turns off. Thus output device 76 provides an output signal for the duration of the triggered state of the monostable circuit.

For switching from the monitor circuit just described to the clean circuit, for cleaning the detection filament 22, control unit 86 includes timer T. It periodically activates switch 80 to break contact with monitor circuit contacts $80_1$ and $80_2$, and make contact with cleaning circuit contacts $80_3$ and $80_4$ for a preset period of time. This connects the monitoring filament to power source 82 through current and resistance limiters, 84 and 88 respectively. By this means a controlled amount of heating power is applied to heat filament 22 in a manner to remove contaminating oil. The General Motors AC L1129 light bulb cited above at 6 volts nominal supply draws about two amperes to give its rated 21 candle power. During a cleaning cycle the current is limited by the current limiter, 84 and held to about seven amperes to produce the cleaning effect. If, instead of being immersed in water the filament is in oil or air a resistance limit, e.g. 0.6 ohms, is imposed by limiter 88. This prevents the filament from overheating and destroying itself or attaining ignition temperature. A typical cleaning cycle would be about 5 seconds, limited on one side by efficiency and on the other by thoroughness. Following cleaning, the detector is once more "asked" as described above if it is in oil or water; i.e. control 86 reactuates switch 80.

Thus limited, the heating current is effective to clean the filament in the manner mentioned, i.e. decreasing the clinging ability of the oil and even emulsifying it through cavitation and sonic cleaning effects accompanied by a "growling" noise, much as a pot on the stove "growls" before rapid boiling is achieved.

Figure 3:
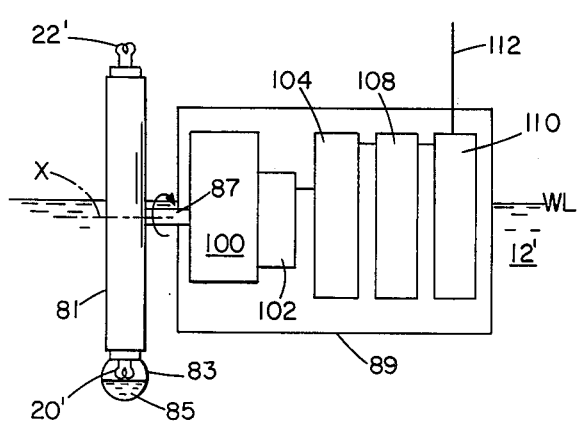
FIG. 3 is a diagrammatic view of another embodiment of an oil detection system in a first and FIG. 4 in a second position.
Figure 4:
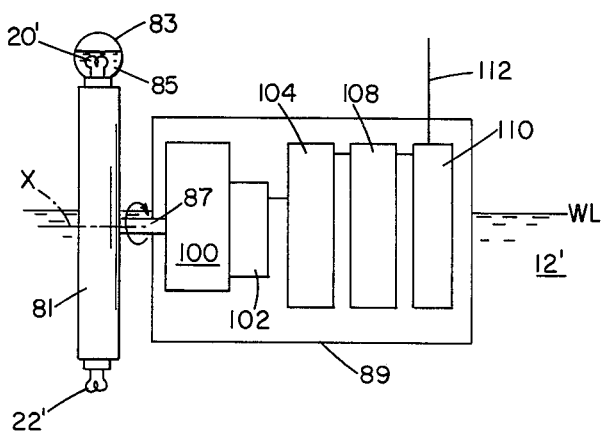

Referring to the embodiment of FIGS. 3 and 4, a support member 81 rotatable about horizontal axis mounts monitoring and reference elements 22', 20' at diametrically opposite ends. Reference filament 20' is in an ampule 83 (i.e., it is a light bulb) only partly filled with water 85 so that in the down position (FIG. 3) the filament is not, and in the up position (FIG. 4) it is, immersed. Support member 81 is mounted on a shaft 87 that protrudes from buoyant support housing 89, and is driven by rotary stepping motor 100. Also in the housing are a potentiometer 102 providing an indication of the rotary position of support 81; electronics 104; logic circuitry 108; and a telemetry transmitter 110 with transmitting antenna 112.

The reference and monitoring filaments 20' and 22' are connected to the electronics 104 by which a pulse of electrical current is periodically generated and difference in resistance of the filaments 20' and 22' is sensed, all as described above. In the position of FIG. 3, the filaments are both exposed to air, covered with film of any liquid to which recently exposed. In this position, both resistance filaments are heated with an electric current pulse and the "water cling" response of reference filament 20' is compared to either the "water cling" or the "oil cling" response of monitoring filament 22'. If monitoring filament 22' has passed through an oil film, oil on its surface will cause the electrical resistance characteristics to be different from the resistance characteristics of reference filament 20'. An output signal indicating the same or the different response is applied to the logic circuitry 108. The support member 81 is then rotated (for example 90° to a position in which the monitoring element 22' is at the surface of the water), another pulse of current is passed through the two elements 20', 22' and the electronics 104 produces another appropriate output. The support member 81 is then rotated to the position shown in FIG. 4, where the reference filament 20' is submerged in water 85 in bulb 83 while the monitoring filament 22' is submerged in the water 12', a pulse is again passed through the filaments and an output is produced. The series of output indications from the electronics 104 is processed by logic circuitry 108, to verify the presence of oil, and the telemetry transmitter 110 is actuated when existence of an oil condition has been established by the logic circuitry 108.

Figure 5:
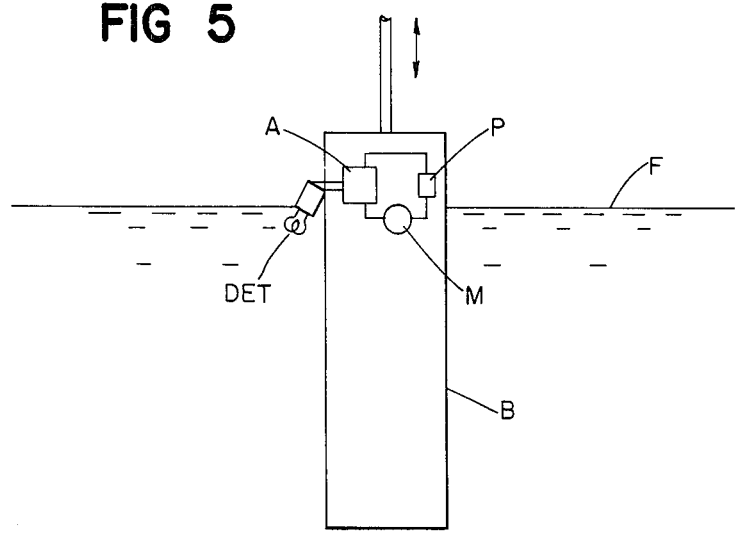

Referring now to FIG. 5, the embodiment of this invention similarly, as before, employs the exposed filament DET of a broken auto tail-lamp, immersed in the test sample, air, oil or water, depending upon the position of probe body B, and the presence or not of oil at the surface F. The circuit A is designed to find out how much current is required to heat the exposed filament to a predetermined temperature. The choice of temperature is limited by safety considerations: it should not be hot enough to ignite oil; on the other hand it should not be cool, so as to give unambiguous readings. A very near or mild red was used in the design of the particular embodiment of FIGS. 5 and 6.

In water it takes an enormous current to heat a filament to mild red. To prevent excessive use of power the current is limited by the power supply P to 5 amperes. This is an ample indication of water when compared with oil's 3 amperes of air's 1 ampere.

It should be underlined that in the embodiment I am simply measuring the amount of power it takes to heat a filament to a given temperature. I have realized that it takes comparatively an enormous amount in water, less in oil, and quite little in air, which leads to an extremely simple detector circuit.

Figure 6:
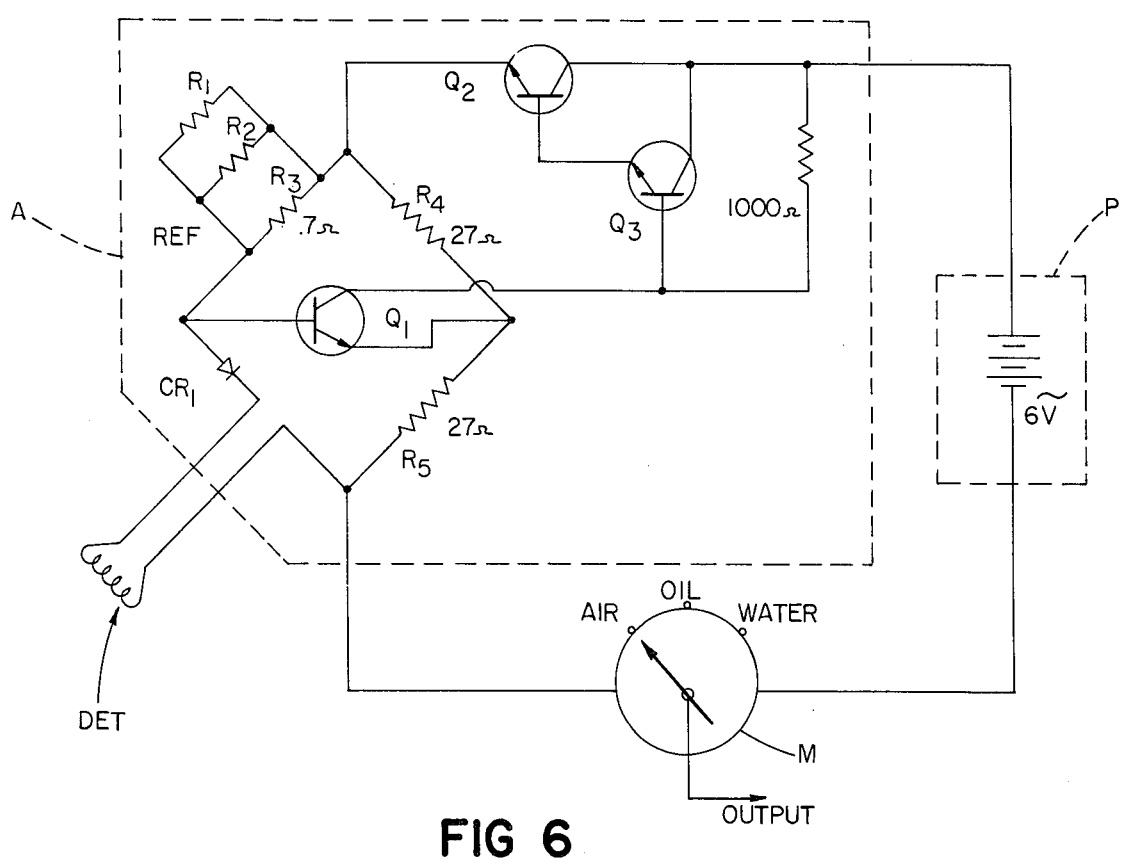
FIG. 6 is a circuit diagram employed in the embodiment of FIG. 5.

Referring to FIG. 6, in this circuit, control of filament current is used to control filament temperature. A network of resistors, e.g. $R_1$, $R_2$ and $R_3$, form reference REF. The reason for showing several resistors in parallel is to show the necessity of employing a reference resistance that will change very little in value with applied current and associated heating. This reference might comprise 15 10 ohm resistors with a total network wattage rating of 50 watts.

Current derived from the darlington amplifier formed by transistors $Q_2$ and $Q_3$ flows through the reference resistance REF, diode CR1 and the exposed lamp filament DET. $Q_1$, bridge-biased by the 27 ohm resistors $R_4$ and $R_5$, controls the flow of current so that when the temperature of the lamp filament DET as exhibited by its terminal potential (its resistance being temperature-dependent) exceeds that of reference REF, $Q_1$ will reduce the current through darlington amplifier $Q_2 Q_3$. Meter M has output points corresponding to oil, air and water.

Those skilled in the art may comment that the gains involved are not sufficient to rigidly discipline current in the filament DET. It must be pointed out that my intention is only to control current sufficiently to indicate air, oil or water, and this circuit is sufficient. Thus ammeter M is readily able to distinguish current produced when filament DET is exposed to oil (e.g. 3 amps) from current produced when exposed to water (e.g. 5 amps, or higher, depending upon the maximum current available from the power source).

It is advantageous that a cleaning circuit as previously described by employed and as will readily be understood, pulsed operation of the unit is advantageous to save power, the tungsten filament as the detector element being particularly suitable for this function. The unit is shown in the form of a gravity-dropped probe for transiting a liquid-air interface, and is capable of use in the other support systems described above.

While the various embodiment shown have been concerned mainly with detecting oil spills or oil films on water it will be understood that certain aspects of the invention apply whenever an oil film may or may not be present on a detector element, in either a fully immersed position or in air.

What is claimed is:

1. A system for detecting different fluids such as oil at the surface of water comprising:
   a monitoring element having a surface exposed for contact with fluid to be monitored, said monitoring element having an electrical current flow characteristic that changes as a function of temperature, and electronic circuitry for heating said monitoring element, said electronic circuitry adapted to apply heating current pulses to heat and produce a temporary increase in temperature of said monitoring element and said electrical circuitry including output means responsive to change in said electrical current flow characteristic during cooling of said monitoring element after termination of said heating to indicate the fluid in contact with said exposed surface.

2. The system of claim 1 wherein said monitoring element is a filament comprising tungsten.

3. The system of claim 1 wherein said monitoring element is positioned at a liquid surface by a buoyant member.

4. The system of claim 1 including a reference element connected in circuit with said monitoring element so that pulses of electrical heating current pass through both elements simultaneously and said output circuitry responds to a differential change between said electrical current flow characteristic of said monitoring and reference elements.

5. The system of claim 4 wherein said monitoring and reference elements are connected in a bridge circuit.

6. The system of claim 1 wherein said output means is adapted to respond to the resistance characteristic of said monitoring element as it cools after the application of a heating current pulse.

7. The system of claim 1 wherein said electronic circuitry includes means for generating a changing signal dependent upon the changing value of said electrical current flow characteristic and an integrator circuit for integrating said signal over a period of time following the application of a heating current pulse, the integrated value representing the change of said current characteristic over said period of time.

8. The system of claim 1 wherein said electronic circuitry further comprises a trigger circuit responsive to said change in said characteristic, said trigger circuit connected to cause said electronic circuitry to again apply a said pulse of heating current to said monitoring element when said change in said characteristic reaches a selected limit due to said cooling, the frequency of occurrence of said heating pulses produced as a result of said trigger output indicating the fluid in contact with said monitoring element.

9. The system of claim 1 wherein said electronic circuitry further comprises a capacitor charged by a battery and switch means for rapidly discharging said capacitor through said monitoring element to produce said pulse of heating current.

10. A system for detecting different fluids such as oil at the surface of water comprising:
a monitoring element having a surface exposed for contact with fluid to be monitored, said monitoring element having an electrical current flow characteristic that changes as a function of temperature, electronic means for applying electrical heating current to said monitoring element, to heat and produce a change in said electrical current flow characteristic of said monitoring element,
output circuitry responsive to said electrical current flow characteristic to produce an output indicating the identity of fluid in contact with said exposed surface, and
means for causing said monitoring element to transit a liquid surface prior to applying said electrical heating current.

11. The system of claim 10 including a driver supported on a housing, said driver effective to move said element relative to said housing to transit said surface.

12. A system for detecting different fluids such as oil at the surface of water comprising:
a monitoring element having a surface exposed for contact with fluid to be monitored, said monitoring element having an electrical current flow characteristic that changes as a function of temperature, electronic means for applying electrical heating current to said monitoring element, to heat and produce a change in said electrical current flow characteristic of said monitoring element,
output circuitry responsive to said electrical current flow characteristic indicating the identity of fluid in contact with said exposed surface, and
circuitry for passing heating current through said monitoring element to clear said exposed surface of oil.

13. The system of claim 12 including circuitry for limiting the electrical parameters of said heating current to prevent ignition of said oil and protect said monitoring element.

14. A system for detecting different fluids such as oil at the surface of water comprising:
a monitoring element having a surface exposed for contact with fluid to be monitored, said monitoring element having an electrical current flow characteristic that changes as a function of temperature, electronic means for applying electrical heating current to said monitoring element, to heat and produce a change in said electrical current flow characteristic of said monitoring element, a reference element connected in circuit with said monitoring element so that said electrical heating current passes through both elements simultaneoulsly,
said reference element being sealed with a reference liquid
and output circuitry responsive to a differential change in resistance of said monitoring and reference elements to produce an output indicating the identity of fluid in contact with said exposed surface.

15. A system for detecting different fluids such as oil at the surface of water comprising:
a monitoring element having a surface exposed for contact with fluid to be monitored, said monitoring element having a resistance characteristic that changes as a function of temperature, circuitry for periodically applying a pulse of electrical heating current to said monitoring element, to heat and produce a change in electrical resistance of the monitoring element,
output circuitry responsive to said electrical resistance indicating the fluid in contact with said exposed surface, and
means for periodically submerging said monitoring element below the surface of water being monitored and for applying said pulse when said element is so immersed.

16. A system for detecting a thin film of oil at the surface of water comprising:
an electrical circuit including a monitoring element and a reference element connected in circuit for simultaneous energization,
said monitoring and reference elements having electrical resistance characteristics that change as a function of temperature, said monitoring element having a surface exposed for contact with a film of oil on the surface of the water to be monitored,
electronic circuitry for heating said monitoring and reference elements, said electronic circuitry adapted to apply heating current pulses to heat both elements simultaneously and produce temporary changes in the electrical resistance of said elements, and said electronic circuitry including output means responsive to a difference between the electrical resistances of said monitoring and reference elements during cooling of said elements after termination of said heating for producing an output indicating that oil is in contact with said exposed surface of said monitoring element.

17. A system for discriminating oil from water comprising:
a monitoring element having a surface exposed for contact with oil in water to be monitored, said monitoring element having a time-temperature characteristic that changes as a function of oil on said exposed surface, first circuitry for periodically applying a pulse of electrical current to said monitoring element to heat and produce a change in an electrical resistance of the monitoring element, output circuitry responsive to a change in said electrical resistance produced by said first circuit for producing an output indicating that oil is in contact with said exposed surface of said monitoring element, and second circuitry for passing heating current through said monitoring element to raise the temperature of said monitoring element for a period longer than the duration of said pulse to clean said exposed surface of oil.

18. The system of claim 17 and further including circuitry for limiting the magnitude of said pulse of heating current.

19. A detector comprising a monitoring device exposed to a surrounding heat absorptive medium, said monitoring device having an electrical characteristic that changes as a funciton of temperature, and electronic means responsive to change in said characteristic of said monitoring device to vary the flow of power to said device, characterized in that said electronic circuit includes reference means representing a predetermined substantially constant desired value for said electrical characteristic of said monitoring device, and said electronic circuit adapted, upon said change in the actual value of said electrical characteristic of said monitoring device, to change said power flow to said monitoring device to restore said actual value of said characteristic of said monitoring device toward said predetermined desired value, and output circuitry responsive to the power flow conditions in said monitoring device to indicate a thermal loss of said monitoring device to said surrounding heat absorptive medium.

20. A system for detecting different fluids such as oil at the surface of water comprising the detector of claim 19, said monitoring device having a surface exposed for contact with fluid to be monitored.

21. The system of claim 20 wherein said monitoring device comprises a filament of tungsten.

22. The system of claim 20 wherein said monitoring device is positioned at a liquid surface by a buoyant member.

23. The system of claim 20 including means for causing said monitoring device to transit a liquid surface prior to detection.

24. The system of claim 20 including circuitry for passing heating current through said monitoring device to clean said exposed surface of oil.

25. The detector of claim 19 wherein the electrical resistance of said monitoring device changes as a function of temperature, said detector including a substantially constant reference resistance and means for applying heating current to said monitoring device until balance is achieved relative to said reference resistance.

26. The system of claim 25 including an amplifier adapted to apply current through said reference resistance and said monitoring device and means responsive to differential current flow therethrough to regulate said amplifier, thereby to control current through said monitoring device in accordance with said reference.

* * * * *